United States Patent [19]

Hass

[11] Patent Number: 4,526,543

[45] Date of Patent: Jul. 2, 1985

[54] FUNCTIONAL DENTAL-BALANCING METHOD AND APPARATUS

[76] Inventor: Martin A. Hass, 11704 Wilshire Blvd., Ste. 222, Los Angeles, Calif. 90025

[21] Appl. No.: 595,930

[22] Filed: Apr. 2, 1984

[51] Int. Cl.³ .............................................. A61C 9/00
[52] U.S. Cl. .................... 433/214; 433/167; 433/229
[58] Field of Search ............... 433/167, 229, 41, 42, 433/43, 44, 45, 25, 68, 140, 214

[56] References Cited

U.S. PATENT DOCUMENTS

| | | | |
|---|---|---|---|
| 1,851,865 | 3/1932 | Ptacek | 128/62 A |
| 2,309,270 | 1/1943 | Opotow | 433/167 |
| 3,084,435 | 4/1963 | Hass et al. | 433/229 |
| 3,488,848 | 1/1970 | Lerman | 433/25 |
| 4,273,532 | 6/1981 | Hass | 433/43 |

Primary Examiner—John J. Wilson
Attorney, Agent, or Firm—Cislo, O'Reilly & Thomas

[57] ABSTRACT

This invention relates to a method and apparatus for functionally balancing the structure of a human mouth. With the method and apparatus of the invention, a pressure equalizing member is utilized wherein an occlusal surface of the posterior teeth of one jaw or denture are covered by a layer of a moldable substance that quickly cures to a hardened shape retaining form. The patient in whose mouth the moldable substance has been placed chews against the resistance offered by the pressure equilizing member so as to engrave the patient's chewing pattern on the opposed occlusal surface of the soft moldable layer. The pressure equalizing member is then removed from the patient's denture and a gap in the occlusal surface is filled with a moldable substance which after hardening overcomes prior art deficiencies to which the invention relates.

3 Claims, 3 Drawing Figures

FUNCTIONAL DENTAL-BALANCING METHOD AND APPARATUS

BACKGROUND OF THE INVENTION

This invention relates to a method and an apparatus for balancing the structure of a human mouth to function in harmony with artificial dentures which have been previously manufactured, for balancing the biting surface of natural human teeth in the jaws, or for balancing an artificial denture during or after its design or manufacture. More specifically, this invention discloses both a method and an apparatus for making a chew-in occlusion on a denture or natural human teeth directly in the human mouth. The method and apparatus of the invention may be used with single denture plates, full denture plates, immediate dentures and bite-opening splints for temporal-mandibular joint treatments where an unbalanced bite has caused joint pains, hearing problems or the like.

As general background, it will be recalled that the lower jawbone is hinged to the skull by a pair of condyles, one at each end of the jawbone, which hingedly seat in sockets shaped and positioned to receive them. The lower teeth in turn are rigidly supported on the hinged lower jawbone. The upper teeth are rigidly positioned in the bone structure of the upper jaw which is fixed with respect to both the hard palate and the rest of the skull.

The surfaces of the upper and lower teeth which come into contact when the mouth is closed to a biting or masticating position are commonly referred to as the occlusal surfaces. If the teeth in one's mouth are not of the correct relative height, that is, if the teeth are too high on one side, the when the occlusal surfaces of the hard teeth come together, there will be a tendency to torque, tilt or lift up on one side of the lower jawbone or of the lower denture. It is extremely important to get the correct bite for inter-engagement of the upper and lower teeth and jaws. It is only when biting occurs back on the molars, during chewing and grinding, that the condyles are seated in bracing position.

It has been found necessary to good health to insure that the condyles are seated equally, whether the teeth be natural or artificial. If the condyles are seated unequally, the person tends to become nervous and there will be a crushing of the membranes in the condyle. A pathological condition of the condyle can thus result from unequalized biting pressures. Earache and hearing difficulties may also be produced.

Specifically, the device of the invention is used to balance tooth occlusion, natural or artificial, enabling it to function in harmony with the Temporal Mandibular Joint (T.M.J.) system during the chewing through the resistance of food, and to seat the denture bases solidly on their ridges simultaneously.

The invention is used in the mouth on newly completed artificial dentures or on dentures which have been previously manufactured, in order to correct for the many processing variables, laboratory discrepancies, acrylic shrinkage, as well as for the deficiencies of steel articulators which cannot duplicate either the complicated human jaw movements or resilient tissue compressions of the gums and joints. In this technique the mouth becomes its own best articulator.

Since all successful dental procedures are dependent upon producing an accurate bite that functions in harmony with the mouth system, it becomes apparent how valuable the device and method of the invention are to dental patients.

In addition to the determination of accuracy of bite recordation for equilibrating completed dentures, the following factors are of utmost importance for patients who wish to lengthen the useful life of their existing dentures using the invention taught herein. The invention is useful in the following non-limiting ways:

1. The disclosed invention makes possible a "new posteriors for old" method where in dentures, new posterior teeth can replace old posterior teeth quickly, by recording and articulating a new air-resistance bite at a corrected vertical closure, and by matching new posterior tooth quadrants set on soft denture acrylic which is then light or pressure cured to hardness. These modified dentures, when returned to the mouth, will have an improved chewing efficiency and give the patient an improved appearance, plus T.M.J. correction, since both the vertical closure and occlusal balance have now been corrected.

2. A new functionally balanced occlusion can also be made by simply adding soft tooth acrylic to the posterior teeth of a denture, recording a functional air-balanced working bite, and hardening the acrylic directly in the mouth by light-curing it. This is a preferred method of the invention, since all the engraved chewing patterns will now be made permanent directly in the mouth without the need for subsequent laboratory adjustments.

These examples of preferred methods of the invention are applicable for full, immediate, single and partial dentures, bite correcting splints for T.M.J. treatments, as well as for making a functional bite for permanent mouth reconstruction, that can be first tested in the mouth for accuracy.

The device of the invention has been clinically developed and tested extensively. In testing the method of the invention, functionally developed three-dimensional working bites have improved the former static, one dimensional air-centric bite technique that was used with regular shellac or plastic base plates (that can bend, slide or tilt on their ridges and ruin an otherwise good bite). The "new posteriors for old" technique described above can be accomplished in one day. The air-balanced functional-retread technique can be done in about thirty minutes.

In general, the method and apparatus of the present invention involves the use of a pressure equalizing member. With the apparatus of the invention in place in the patient's mouth, the occlusal surface of the posterior teeth of one denture is covered with a layer approximately 1 to 3 millimeters thick of a moldable substance such as self-curing or light curing tooth acrylic that is capable of curing to a hardened shape retaining form. The patient is then instructed to close his jaws and chew naturally against the resistance offered by the pressure equalizing member. The pressure equalizing member creates the same resistance the mouth system would encounter in chewing food. The chewing pattern of the opposed occlusal surfaces is directly engraved in the soft, moldable layer which is permitted to cure in place to make the corrected chew-in occlusion permanent. The pressure equalizing member is then removed from the patient's mouth and the gap in the occlusal surface that was covered by the pressure equalizing member is filled in with the same moldable substance. The gap area is now formed by having the patient bite downward against the previously hardened chew-in occlusal surface. The resulting chew-in occlusal surface will now function in perfect harmony with the mouth, bone, teeth and dental system.

Thus, unlike prior art dental balancing systems and devices, such as those claimed in U.S. Pat. No. 3,084,435 to Hass, et al., the present invention discloses a method and an apparatus that permits the correction or fabrication of a chew-in occlusion directly in the patient's mouth on completed dentures within minutes instead or merely taking a one dimensional centric measurement of the nature of the bite and later performing a repeated process of adjustment/measurement until a condition of a balanced occlusion spacing hopefully prevails.

The present invention eliminates the need for prior art trial-and-error method of measurement, followed usually by a laboratory adjustment and remeasurement until an acceptable fit is achieved. The present invention, unlike the prior art, also permits the fabrication of a customized chew-in occlusion directly in the mouth or recording a bite for a "new posterior teeth for old occlusion," wherever the patient may be or in whatever position the patient may be confined in, within a matter of minutes. This is an improvement over existing prior art in that elderly denture patients confined in hospital beds or the like who are unable to sit upright or to visit a dental office may now be fitted directly in their hospital beds in prone or reclining positions, so that they can have teeth that they can chew with.

OBJECTS AND SUMMARY OF THE INVENTION

It is an object of the invention to provide a method and apparatus for shaping the occlusal surfaces of the teeth or dentures to provide a biting action in which the condyles are properly seated and balanced in their sockets and the denture based are seated solidly on their ridges.

It is a further object of the invention to provide a method and apparatus for designing artificial dentures to ensure that they will be properly balanced to function in harmony with all the movements of the mouth-joint system.

It is still yet another object of this invention to provide a means for fabricating a customized chew-in occlusion directly in the mouth wherever the patient may be or in whatever position the patient may be confined in.

It is still yet another object of this invention to provide a method for fabricating a customized new tooth occlusion on a patient's existing dentures that is less costly than purchasing new dentures, and benefits the patient with improved appearance, chewing efficiency and general health.

It is a further object of this invention to provide a means for balancing a T.M.J. (Temporal Mandibular Joint) treatment splint by making a chew-in occlusion on it directly in the human mouth which splint is positioned in the mouth to function as a true center-bearing pivot, in order to harmonize the occlusion with the joint function.

It is yet another object of this invention to provide a method and apparatus using a flexible resilient member which is, in effect, seated in the mouth and partially covers a portion of the occlusal surface of a denture or a splint so that the occlusal surfaces may be shaped to seat snugly and exactly one against the other, when the mouth system is properly air-balanced.

Other objects, features, and advantages of the present invention will become more fully apparent to those skilled in the art from the following detailed description taken in connection with the accompanying drawings.

DESCRIPTION OF THE BEST EMBODIMENTS CONTEMPLATED

Figure 2:
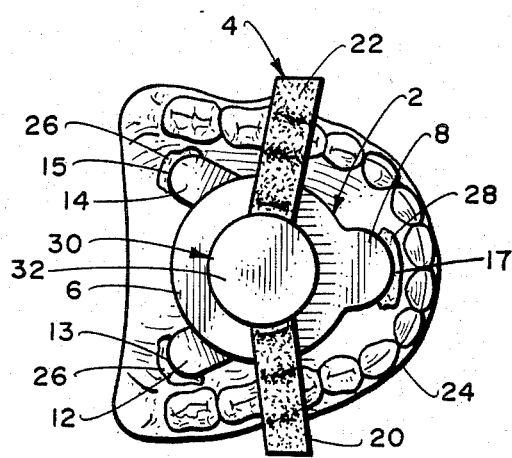
FIG. 2 is a bottom plan view of the apparatus of the invention as it would be in position in the mouth for balancing the teeth structure.

The preferred embodiment of the apparatus of the invention illustrated in the drawings, has a bearing plate, preferably in the form of tripod support member 2, annular in configuration and of a size to fit into a human mouth which is provided with a planar surface 3 having an aperture 10. A flexible, resilient spacer member 4 having extended elongated portions 20 and 22 is mounted on tripod support member 2 in a selectively removable manner by conventional means, such as pin 30 having an enlarged head portion 32 and an extended opposite end portion 34 adapted to pass through aperture 5 of spacer member 4 and be received and retained in aperture 10 in planar surface 3. In use, enlarged head portion 32 of pin 30 engages spacer member 4 and retains it in a fixed but selectively removable relation to tripod support member 2.

When spacer member 4 is to be removed, pin 30 is withdrawn from aperture 10 of planar surface 3 thereby releasing spacer member 4 from engagement with planar surface 3 of tripod support member 2. End portion 34 of pin 30 is now withdrawn from aperture 5 of spacer member 4 and a replacement spacer member may be used by inserting pin 30 through the aperture in the replacement spacer member and then into aperture 10 in planar surface 3. Spacer member 4 may be removed for hygenic or wear replacement purposes.

The flexible, resilient spacer member 4 may be formed from resilient closed cell material and, in the preferred embodiment, may be fabricated from closed cell polyethylene or any similar suitable Federal Food and Drug Administration approved material of about 5/16 inch thickness. Resilient spacer member 4 uses the confined gas (usually air) in its closed cell structure to exert and transmit an even resistance to compressive forces applied to it due to the known fact that a confined gas exerts pressure equally.

Extended, elongated portions 20 and 22 of resilient spacer member 4 extend in an angular fashion, so that they may be rotatably positioned to adapt to various mouth and jaw sizes. A preferred angular range for the extended, elongated portions 20 and 22 would be from about 15 to 60 degrees from an axis perpendicular to the longitudinal axis X—X of main body portion 6 of tripod support member 2.

Figure 3:
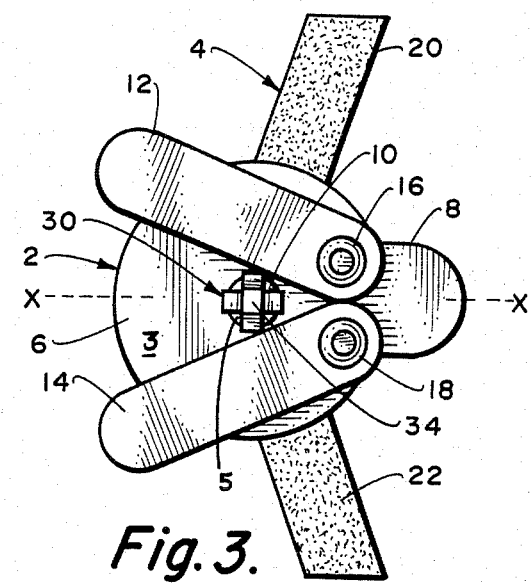
FIG. 3 is a top plan view of the apparatus of the invention.

As may be most clearly seen in FIGS. 2 and 3, tripod support member 2 comprises a substantially circular main body section 6. At one end of this main circular section is a substantially semi-circular protrusion 8 which is adapted to be seated in the forward portion of the mouth. The aperture 10 is located at the center of main body section 6. The projected longitudinal axis X—X of protrusion 8 extends through the center of aperture 10. Tripod support member 2 is further provided with a pair of pivotally mounted arms 12 and 14. These arms 12 and 14 may be mounted for pivotal movement on planar surface 3 of tripod support member 2 in a plane parallel to the plane of planar surface 3 by any conventional means, such as the rivets 16 and 18 in tripod support member 2. Preferably, rivets 16 and 18 are spaced equally from longitudinal axis X—X and are equally radially spaced from the center of main body section 6.

Each of the pivotally mounted arms 12 and 14 is of a dimension and position such that it extends beyond the edge of the tripod support member 2. In the illustrative embodiment shown in the drawings, the arms 12 and 14 are located adjacent each other near the base of protrusion 8 at the forward portion of main body portion 6 of tripod support member 2. The arms 12 and 14 extend in a generally rearward direction and may be swung outwardly from longitudinal axis X—X of main body portion 6 of tripod support member 2 sufficient to seat at the edges of the patient's mouth or dentures. Of course, the pivotal arrangement permits adjustment of the tripod support member 2 to mouths of varying configurations or sizes.

Figure 1:
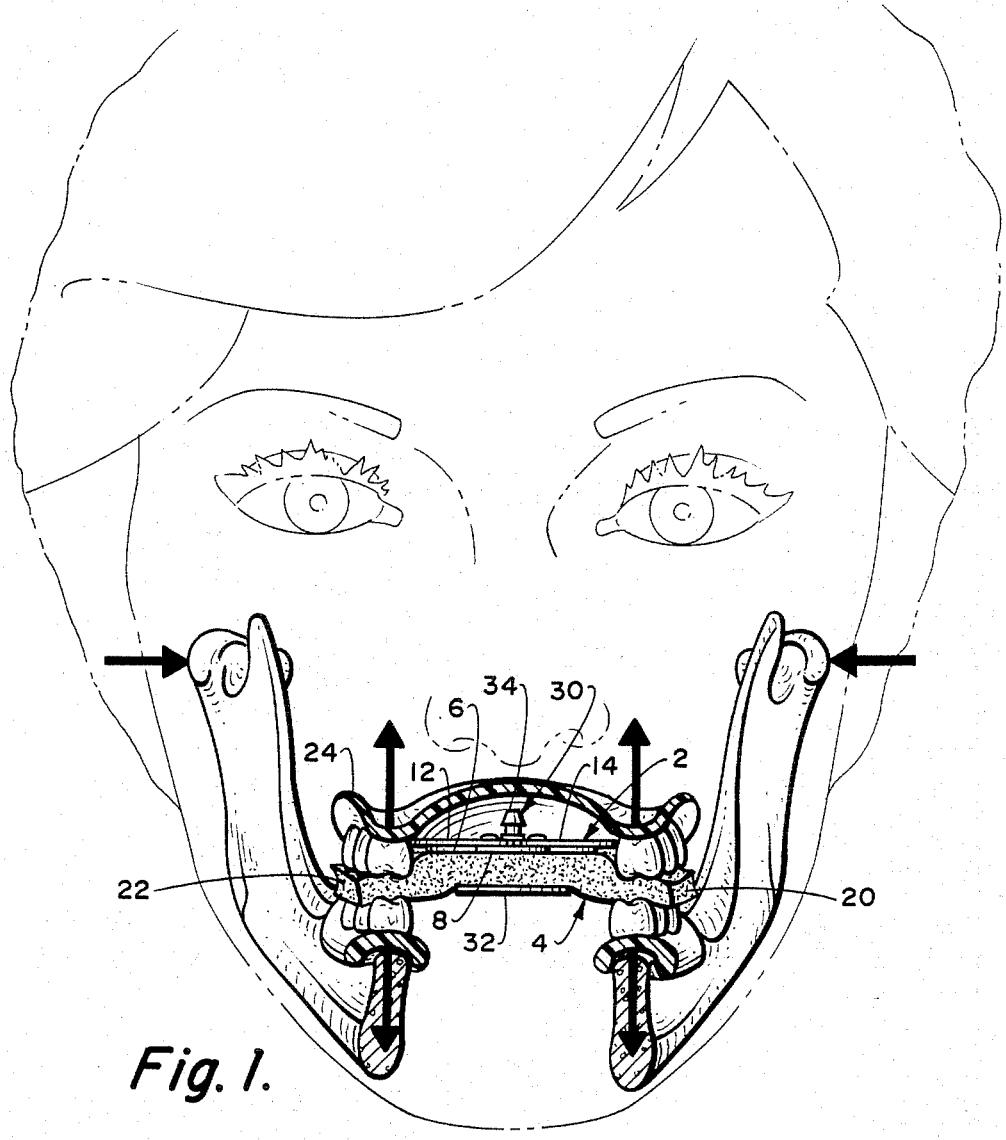
FIG. 1 is a cross-sectional view showing, in phantom line, a patient having the apparatus of the invention in position for balancing the mouth structure.

The manner in which the resilient spacer member 4 and tripod support member 2 are inserted into the mouth for use is best seen in FIGS. 1 and 2. It will be noted from FIG. 2 in particular, that the tripod support member 2 may be positioned on the upper jaw with its adjacent arms 12 and 14 on the upper side adjacent to the roof of the patient's mouth. The edge of each arm 12 and 14 is temporarily secured to the upper denture 24 by sealing, sticky or adhesive wax 26 which secures the end of each arm to denture 24. Similarly, the piece of wax 28 is used to secure the protrusion 8 to the forward central portion of denture 24. It is thus seen that the tripod support member 2 is secured and supported at these three points 13, 15, 17 to the denture 24, thus affording a stable mount for the tripod support member 2. These three points 13, 15, 17 as may be seen in FIG. 2, are the ends of the two arms 12 and 14 which are supported on opposite sides at the rear of the mouth near the molars and the front protrusion 8 which is supported at the central forward position of the mouth in back of the teeth. Preferably, protrusion 8 is placed at the center of the mouth, whereas points 13 and 15 are placed on opposite sides of the mouth and equally spaced from longitudinal axis X—X.

It will, of course, be apparent that denture 24, although shown as a conventionally completed denture could also be the wax or acrylic form used in preliminary fittings in the design and manufacture of the denture. Furthermore, the method and apparatus of this invention are also applicable to the adjustment and balancing of removable Temporal-Mandibular Joint (T.M.J.) splints made on natural teeth. In any of these applications or models of operation, the tripod support member and flexible resilient spacer member are used in substantially the same manner shown in the drawings. Where the natural teeth are involved, the tripod support member may be attached directly to the T.M.J. splint rather than to the denture plate.

When dentures are being fitted to customize the chew-in occlusion of the dentures, the upper and lower dentures approximately fit the patient's mouth. The tripod support member is anchored to one of the denture plates (as a non-limiting example for discussion purposes, the upper denture plate), with the wing-like closed air cell resilient spacer member positioned between and partially covering the occlusal surfaces of the teeth. The uncovered occlusal surfaces of the teeth are then covered with a layer of biomedical substance which is applied in a soft conformable state but which cures to a hardened conformed state in a relatively short period. As a non-limiting example, such a material as dental soft acrylic that can be light cured, self cured or pressure cured is preferred for use. While the thickness of the layer of biomedical substance must, of necessity, vary from patient to patient, it is preferred to have this layer vary from about 1 mm to about 3 mm in thickness.

Once the tripod support member, the wing-like closed air cell resilient spacer member, and the layer of conformable material are in place, the patient is instructed to bite down and chew naturally on the elongated portions 20 and 22 of the resilient spacer member 4 between the upper and lower occlusional surfaces of the teeth. It is known, as a general law of physics, that a confined gas, such as the air confined in the closed cell structure of the flexible resilient spacer member when subjected to pressure, will exert equal pressure in all directions. Accordingly, when the patient bites down and chews naturally on the flexible resilient spacer member portions 20 and 22 located between the pivotal occlusal surfaces of his molar teeth, the lower and upper denture plates will be solidly driven against their respective gums. This tends to balance both the upper and lower base plates of the dentures, and the condyles in their sockets.

With the mouth system in balance, the soft conformable material on the occlusional surfaces is engraved and molded to a perfectly balance chew-in occlusion while in the patient's mouth. The material is now allowed to harden to its permanently conformed shape (in the case of self-cure tooth acrylic, the material hardens while the patient chews, within a matter of minutes).

Once hardened, the flexible resilient spacer member and the tripod support member are removed from the patient's mouth. The occlusal surface, previously covered by the extending wing-like portions 20 and 22 of the flexible resilient spacer member, is now filled in with more of the soft conformable substance and the patient is again instructed to chew naturally until the newly added material hardens. There is no need for having the extending wing-like portions 20 and 22 of the flexible resilient spacer member between the occlusional surfaces during the second chewing as the previously hardened material provides a corrected chew-in occlusion and only a small gap portion remains to be formed.

The patient's denture is now checked to remove any burrs, spillover, or the like of the now hardened material. The patient now has a customized chew-in occlusion perfectly balanced to the unique characteristics of his mouth system in one, quick setting that does not require repeated, time consuming fittings followed by the necessity of sending the dentures to a laboratory for articulation and processing, all of which have the potential for errors.

It will be noted that the present method and apparatus is particularly applicable to the balancing of natural teeth or finished dentures as well as to the original design of dentures. The present method relies upon the natural centering of the jaws without any restraints other than the pressure restraints of closing. No forward-backward, anterior-posterior or lateral restraint is placed on the jaws, so the jaws will automatically tend to center brace and chew instinctively. The present method uses no tubes or other apparatus protruding from the front of the mouth, but relies upon the basic reflexes of chewing and bracing, which, when undisturbed, will naturally position the jaws in functional, working alignment.

In practice, the balancing method disclosed herein finds its greatest application to the balancing of teeth of existing dentures. This results from the fact that, since the human organism is continually growing and changing, the shape of the gums similarly tends to change. With advancing age, the gums, particularly of a person wearing a denture, tend to shrink. It is therefore desirable that periodically, as frequently as once a year, for example, the balance of the teeth should be tested and adjusted by rebalancing, if necessary. Of course, if the change is severe, as in the case of immediate dentures, where there is considerable change in the first few months, then the apparatus of the invention can also be used during the course of relining the dentures.

Both an apparatus and testing program in accordance with the invention disclosed herein have been used in empirical analysis of the system disclosed herein, and are described below as a non-limiting example of both the apparatus and method aspects of the invention.

The apparatus of the invention was also used in conjunction with the method of the invention to fabricate a chew-in occlusion on dentures directly in the mouth for elderly patients who were confined to wheel chairs or in convalescent homes and unable to undergo prior art treatments.

The patients were first fitted with the apparatus of the invention and the method taught herein was applied using sticky wax to seat the apparatus and dental soft acrylic compound as the conformable material. It was found that many of the patients were successfully treated in the prone or supine position on their beds. Similarly, the entire process from start to finish was carried out at the patient's bedside within a short period of time, typically twenty to thirty minutes, and did not require any repeated measurement or laboratory readjustment. Other patients benefitted from the "new posterior teeth for old" technique.

While a particular exemplary preferred embodiment of the invention has been described in detail above, it will be understood that modifications and variations therein may be effected without departing from the true spirit and scope of the novel aspects of the present invention, as defined by the following claims.

I claim:

1. The method of balancing natural and denture teeth by making a chew-in occlusion directly in a human mouth comprising the steps of:
   (a) Placing a resilient member in the mouth positioned to cover for right and left corresponding partial portions of the occlusal surfaces of the teeth;
   (b) Covering the uncovered occlusal surfaces of the teeth on one jaw with a conformable substance that hardens to a permanent conformed shape;
   (c) Urging the upper and lower jaws to chew naturally against said resilient member to form the conformable shape;
   (d) Removing said resilient member from the mouth after said conformable substance has hardened;
   (e) Filling in the occlusal surface formerly covered by said resilient member with more of said conformable substance;
   (f) Urging the upper and lower jaws together to form said conformable substance covering the occlusal surface formerly covered by said resilient device and hardening said conformable substance.

2. The method of balancing natural and denture teeth in a human mouth comprising the steps of:
   (a) Restraining closing movement of the jaws by means of a flexible resilient member positioned in the mouth to partially cover a portion of the corresponding right and left occlusal surfaces of the teeth and acting to apply a restaining self-balancing force against the occlusal surfaces of the teeth to duplicate food chewing resistance;
   (b) Covering the uncovered occlusal surfaces of the teeth on one jaw with a conformable substance that hardens to a permanent conformed shape;
   (c) Moving the jaws together in a natural chewing movement against the restraint of said resilient member until said conformable substance has cured to a hardened form;
   (d) Removing said resilient member from the mouth after said conformable substance has hardened;
   (e) Filling in the occlusal surface formerly covered by said resilient member with said conformable substance; and,
   (f) Moving the jaws together in a natural chewing movement to form said conformable substance covering the occlusal surface formerly covered by said resilient member and hardening said conformable substance.

3. The method of balancing a bite opening Temporal-Mandibular Joint splint in a human mouth comprising the steps of:
   (a) Mounting an acrylic splint on a patient's lower natural teeth leaving uncovered the occlusal surfaces of the opposing jaw, moving with its respective jaw and permitting complete freedom of movement of said jaws, having a resilient member mounted therein adapted to interpose between the upper and lower occlusal surfaces, and partially covering said occlusal surface to provide a balanced restraining force opposing the closing of the jaws while permitting unrestrained lateral and interior-posterior movement of said jaws;
   (b) Covering the occlusal surface of the splint with a conformable substance that hardens to a permanent conformed shape;
   (c) Closing said jaws in a natural chewing movement against said resilient member to engrave the occlusal surfaces of the upper teeth to space said surfaces evenly as the jaws are moved together against the restraint of said resilient member thereby engraving and forming said conformable substance covering said occlusal surface of the splint on which said rigid member is mounted;
   (d) Removing said resilient member from the splint after said conformable substance has hardened;
   (e) Filling in the occlusal surface of the splint formerly covered by said resilient member with said conformable substance;
   (f) Moving the jaws together in a natural chewing movement to form said conformable substance covering the occlusal surface of the splint formerly covered by said resilient member;

(g) Hardening the bite pattern which is engraved into the soft acrylic which was placed on the occlusal surface of the acrylic splint;
(h) Trimming and polishing the new functionally balanced splint occlusion;
(i) Placing the splint over the lower natural teeth to produce a bite opening occlusion for the treatment of Temporal-Mandibular Joint problems that stem from condylar dysfunction resulting from a previous occlusal imbalance.

* * * * *